United States Patent [19]

Effland et al.

[11] Patent Number: 5,686,626

[45] Date of Patent: Nov. 11, 1997

[54] 1,3-DIHYDRO-1-AMINO-2H-INDOL-2-ONES

[75] Inventors: Richard C. Effland, Bridgewater; David G. Wettlaufer, Phillipsburg, both of N.J.

[73] Assignee: Hoechst Marion Roussel, Inc., Cincinnati, Ohio

[21] Appl. No.: 431,526

[22] Filed: Apr. 28, 1995

Related U.S. Application Data

[62] Division of Ser. No. 243,654, May 13, 1994, Pat. No. 5,464,846, which is a continuation of Ser. No. 961,947, Oct. 16, 1992, abandoned, which is a division of Ser. No. 736,366, Jul. 26, 1991, Pat. No. 5,179,119, which is a division of Ser. No. 535,640, Jun. 11, 1990, Pat. No. 5,053,511, which is a continuation-in-part of Ser. No. 388,437, Aug. 2, 1989, Pat. No. 5,006,537.

[51] Int. Cl.$^6$ .................................................. C07D 209/02
[52] U.S. Cl. ...................................................... 548/483
[58] Field of Search ........................................... 548/483

[56] References Cited

U.S. PATENT DOCUMENTS

| | | | |
|---|---|---|---|
| 3,975,531 | 8/1976 | Welstead, Jr. et al. | 514/416 |
| 4,182,774 | 1/1980 | Welstead, Jr. et al. | 514/539 |
| 4,260,767 | 4/1981 | Dusza | 546/306 |
| 5,064,852 | 11/1991 | Howard, Jr. et al. | 514/409 |

FOREIGN PATENT DOCUMENTS

| | | |
|---|---|---|
| 0164860 | 12/1985 | European Pat. Off. |
| 0287982 | 10/1988 | European Pat. Off. |

OTHER PUBLICATIONS

CA 112:178841, Zey et al. 1990.

V.B. Avdeyev, et al., Khimiya Geterotsiklicheskikh Soedinenii, 524 (1983) published in the Soviet Union and entitled "6–Substituted–1–Heterocyclic Arylamino–3–Arylhydroxyindoles" and English translation thereof.

H.E. Baumgarten, et al., 82, 3977 (1960) published in the United States of America and entitled "Cinnolines. VI. The Structure of Neber's Lactam. A New Synthesis of 3–Cinnolinol:".

G. Winters, et al., Chemical Abstracts, 102, 78764w (1985) published in the United States of America and entitled "Synthesis and pregnancy terminating activity of pyrazolo [1,5–a]indols and quinolines".

*Primary Examiner*—Jane Fan
*Attorney, Agent, or Firm*—Raymond R. Wittekind; Barbara E. Kurys

[57] ABSTRACT

This invention relates to 1,3-dihydro-1-(pyridinylamino)-2H-indol-2-ones of the formula

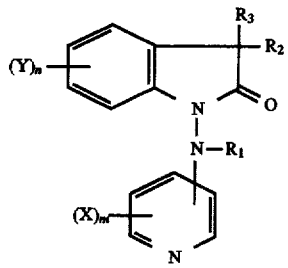

where $R_1$, $R_2$ and $R_3$ are independently hydrogen, loweralkyl, aryl, arylloweralkyl or heteroarylloweralkyl selected from the group consisting of pyridinylmethyl, pyridinylethyl, thienylmethyl, thienylethyl; or $R_2$ and $R_3$ together form a cycloalkane ring of 4 to 6 carbons or a spiro-fused aryl cycloalkane or heterocycloalkyl selected from the group consisting of piperidine and tetrahydropyran; X and Y are independently hydrogen, halogen, hydroxy, loweralkyl, loweralkoxy, nitro, amino or trifluoromethyl; m and n are independently integers of 1 to 3, the pharmaceutically acceptable acid addition salts thereof and, where applicable the optical, geometrical and stereoisomers and racemic mixtures thereof. The compounds of this invention display utility as analgesics, anticonvulsants, for enhancing memory and for the treatment of Alzheimer's disease.

3 Claims, No Drawings

1,3-DIHYDRO-1-AMINO-2H-INDOL-2-ONES

This is a division of prior application Ser. No. 08/243,654 filed May 13, 1994, now U.S. Pat. No. 5,464,846 which is a continuation of application Ser. No. 07/961,947 filed Oct. 16, 1992, now abandoned, which is a division of application Ser. No. 07/736,366 filed Jul. 26, 1991, now U.S. Pat. 5,179,119, which is a division of application Ser. No. 07/535,640 filed Jun. 11, 1990, now U.S. Pat. No. 5,053,511 which is a continuation-in-part of application Ser. No. 07/388,437 filed Aug. 2, 1989, now U.S. Pat. No. 5,006,537.

This invention relates to compounds of the formula

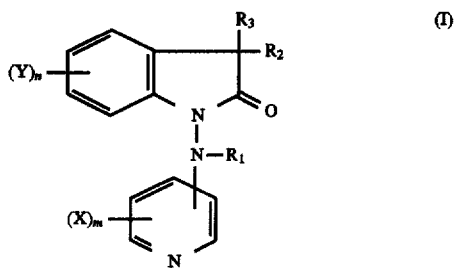

where $R_1$, $R_2$ and $R_3$ are independently hydrogen, loweralkyl, aryl, arylloweralkyl or heteroarylloweralkyl selected from the group consisting of pyridinylmethyl, pyridinylethyl, thienylmethyl, thienylethyl; or $R_2$ and $R_3$ together form a cycloalkane ring of 4 to 6 carbons or a spiro-fused aryl cycloalkane or heterocycloalkyl selected from the group consisting of piperidine and tetrahydropyran; X and Y are independently hydrogen, halogen, hydroxy, loweralkyl, loweralkoxy, nitro, amino or trifluoromethyl; m and n are independently integers of 1 to 3, the pharmaceutically acceptable acid addition salts thereof and, where applicable the optical, geometrical and stereoisomers and racemic mixtures thereof. The compounds of this invention display utility as analgesics, anticonvulsants, for enhancing memory and for the treatment of Alzheimer's disease.

Preferred embodiments of the invention are those of Compound I where $R_1$ is selected from hydrogen and loweralkyl; $R_2$ is selected from hydrogen and loweralkyl; $R_3$ is selected from hydrogen and loweralkyl.

Most preferred embodiments of the invention are those of Compound I where $R_1$ is selected from loweralkyl; $R_2$ is selected from hydrogen; and $R_3$ is selected from hydrogen.

This invention also relates to compounds of the formula

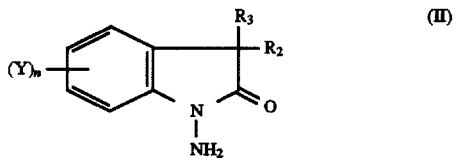

where $R_2$, $R_3$, Y and n are as previously defined, which are useful as intermediates for the preparation of the target compounds of this invention.

Throughout the specification and the appended claims, a given chemical formula or name shall encompass all optical, geometrical and stereoisomers thereof and racemic mixtures where such isomers and mixtures exist, as well as pharmaceutically acceptable acid addition salts thereof and solvates thereof such as hydrates.

In the above definition, the term "lower" means the group it is describing contains from 1 to 6 carbon atoms. The term "alkyl" refers to a straight or branched chain hydrocarbon containing no unsaturation, e.g., methyl, ethyl, isopropyl, t-butyl, neopentyl, n-hexyl, etc.; the term "arylloweralkyl" refers to a monovalent substituent which consists of an "aryl" group e.g., phenyl, o-tolyl, m-methoxyphenyl, etc., as defined by the formula

where Z is as defined below, and m is an integer of 1 to 3, linked through a loweralkylene group having its free valance bond from a carbon of the loweralkylene group, and having a formula of

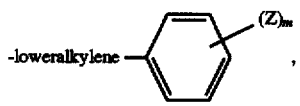

where Z is hydrogen, halogen, loweralkyl, loweralkoxy, $CF_3$, $NO_2$ and $NH_2$, OH and m is as previously defined; the term "alkylene" refers to a bivalent radical of the lower branched or unbranched alkyl group it is derived from having valence bonds from two terminal carbons thereof; e.g., ethylene ($-CH_2CH_2-$), propylene ($-CH_2CH_2CH_2-$), isopropylene

etc.; the term "heteroaryl" refers to a aromatic heterocyclic mono- or bicyclic radical, e.g., pyridinyl, thiophene, etc.; and the term "heteroarylloweralkyl" refers to a loweralkyl group having a heteroaryl substituent thereon; the term "alkoxy" refers to a monovalent substituent which consists of an alkyl group linked through an ether oxygen having its free valence bond from the ether oxygen, e.g., methoxy, ethoxy, propoxy, butoxy, pentoxy, etc.; and the term "halogen" refers to a member of the halogen family consisting of fluorine, chlorine, bromine and iodine.

The compounds of the present invention are prepared in the following manner. The substituents are as defined above unless indicated otherwise.

A 1-aminooxindole having the formula

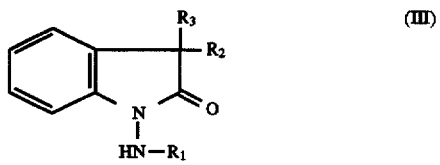

where $R_1$ is hydrogen or loweralkyl, in solution with a loweralkanol or phenolic solvent, i.e., phenol, isopropanol, butanol, etc., is reacted with an optionally substituted halopyridine hydrochloride of the formula

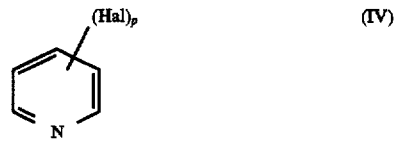

where Hal is halogen and p is 1 or 2, to afford Compound I of the invention of the formula

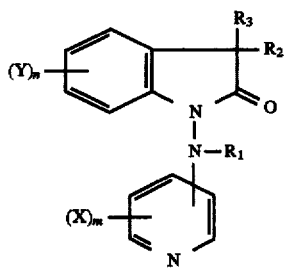

(I)

The 1-aminooxindole, Compound III, is typically synthesized utilizing procedures described in Baumgarten et al., *J. Am. Chem. Soc.* 82, 3977–42 (1960), which discloses the formation of 1-aminooxindole by the reduction of 3-cinnolinol with zinc and $H_2SO_4$ and by thermal cyclization of o-hydrazinophenylacetic acid.

Typically, the formation of Compound I is conducted under an inert atmosphere, i.e., nitrogen or argon, at a temperature of 80° C. to 150° C. for ½ to 24 hours.

To prepare Compound I where $R_1$=alkyl, 1-aminooxindole is reacted with a lower alkyl aldehyde, such as propionaldehyde, in the presence of a catalyst, i.e., p-toluenesulfonic acid to afford Compound V of the formula

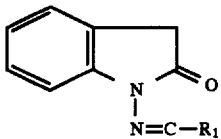

(V)

Compound V is in turn reduced with sodium cyanoborohydride ($NaBH_3CN$) to afford Compound VI of the formula

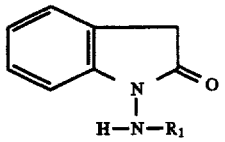

(VI)

This reaction typically takes place in an lower alkanol solvent, i.e., methanol, at a temperature of 0° to 50° C. for 0.25 to 6 hours. The reduction using $NaBH_3CN$ is described in Borch et al., *J. Am. Chem. Soc.*, 93, 2897, 1971.

Compound VI is reacted with a halopyridine hydrochloride i.e., 4-bromopyridine HCl or 4-chloropyridine HCl to give Compound I, where $R_1$=alkyl.

Compounds of the present invention are useful as analgesic agents due to their ability to alleviate pain in mammals. The activity of the compounds is demonstrated in the phenyl-para-quinone writhing assay in mice, a standard assay for analgesia [*Proc. Soc. Exptl. Biol. Med.*, 95, 729 (1957)]. Presented in Table 1 is the analgesic effect of some of the compounds of the invention expressed as either the subcutaneous dose at which 50% of the phenyl-para-quinone induced writhing is inhibited in the animals, i.e., the $ED_{50}$ value, or as the % decrease in writhing at a given dose.

TABLE 1

| Compound | $ED_{50}$ or % Inhibition of Writhing |
|---|---|
| 1,3-Dihydro-1-(4-pyridinyl-amino)-2H-indol-2-one | $ED_{50}$ = 0.69 mg/kg, s.c. |
| 1,3-Dihydro-1-(propyl-4-pyridinyl-amino)-2H-indol-2-one | −58% at 20 mg/kg, s.c. |
| Salicylic Acid (standard) | $ED_{50}$ = 3.28 mg/kg, s.c. |

The analgesic relief of pain is achieved when the compounds of the invention are administered to a subject requiring such treatment at an effective oral, parenteral or intravenous dose of from 0.01 to 100 mg/kg of body weight per day. A preferred effective dose within this range is from about 10 to 50 mg/kg of body weight per day. A particularly preferred effective amount is about 30 mg/kg of body weight per day. It is to be understood, however, that for any particular subject, specific dosage regimens should be adjusted according to the individual need and the professional judgment of the person administering or supervising the administration of the compound. It is further to be understood that the dosages set forth herein are examples only and that they do not, to any extent, limit the scope or practice of the invention.

The compounds of the present invention are also useful in the treatment of various memory dysfunctions characterized by decreased cholinergic function such as Alzheimer's Disease. This utility is demonstrated in the Dark Avoidance Assay.

Dark Avoidance Assay

In this assay, mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chambers, the animal re-enters the dark compartment shortly after being placed in the test chamber 24 hours later. The effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Presented in Table 2 is the activity of some of the compounds of the invention in this assay.

TABLE 2

| Compound | Dose (mg/kg of body wt) | % of Animals With Scopolamine Induced Memory Deficit Reversal |
|---|---|---|
| 1,3-Dihydro-1-(4-pyridinylamino)-2H-indol-2-one | 0.31 | 27 |
|  | 0.63 | 27 |
|  | 1.25 | 27 |
| 1,3-Dihydro-1-(propyl-4-pyridinylamino)-2H-indol-2-one | 1.25 | 27 |
| 1,3-Dihydro-1-(3-fluoro-4-pyridinylamino)-2H-indol-2-one | 1.0 | 27 |
|  | 3.0 | 27 |
| 1,3-Dihydro-3,3-dimethyl-1-(propyl-4-piperidinylamino)-2H-indol-2-one | 0.3 | 20 |
| 1,3-Dihydro-1-[(3-fluoro-4-pyridinyl)amino]-3-methyl-2H-indol-2-one hemifumarate | 0.3 | 27 |
|  | 3.0 | 20 |
| 1,3-Dihydro-3,3-dimethyl-1-[4-(3-fluoropyridinyl)-propylamino]2H-indol-2-one | 0.3 | 21 |
|  | 1.0 | 27 |
| 1-Amino-3,3-bis(4-pyridinylmethyl)-1,3-dihydro-2H- | 0.3 | 21 |

TABLE 2-continued

| Compound | Dose (mg/kg of body wt) | % of Animals With Scopolamine Induced Memory Deficit Reversal |
|---|---|---|
| indol-2-one | | |
| 1-Amino-1,3-dihydrospiro-[2H-indene-2,3'-[3H]-indol]-2'(1'H)one | 0.3<br>1.0 | 21<br>20 |
| 1,3-Dihydro-1'-(propyl-4-pyridinylamino)spiro[2H-indene-2,3'-[3H]indol]-2'(1'H)-one | 3.0 | 25 |
| 1'Methyl-1-(propyl-4-pyridinylamino)spiro-[3H-indole-3,4'-piperidin]-2(1H)-one | 1.0 | 20 |
| 1,3-Dihydro-1-[(3-fluoro-4-pyridinyl)-propylamino]-2H-indol-2-one | 0.3<br>3.0 | 20<br>20 |
| Tacrine (standard) | 0.63 | 13 |
| Pilocarpine (standard) | 1.25 | 19 |

The compounds of the invention are also useful as anticonvulsants due to their anticonvulsant activity in mammals. Anticonvulsant activity is measured in the male mouse using the supramaximal electroshock (SES) assay described in *Arch. Int. Pharmacodyn.* 92:97–107, 1952. In this procedure, groups of male mice (Charles River, CD-1, 18–30 gm) are used. Drugs are prepared using distilled water and, if insoluble, a surfactant is added. Control animals receive vehicle. Drugs are routinely administered interperitoneally (i.p.) The dosage volume is 10 ml/kg. A primary screen is given a 30 minute pretreat. The animals' eyes are placed across the output terminals of an A.C. shocker that delivers 206 volts rms for 300 msec. Electrode paste coats the animals' eyes at the point of contact with the terminals. A compound is considered to give protection if the mouse does not exhibit extensor tonus. Protection is expressed as normalized percent inhibition relative to vehicle control.

The anticonvulsant activity of some of the compounds of this invention is given below in Table 3.

TABLE 3

| Compound | $ED_{50}$ mg/kg i.p. |
|---|---|
| 1,3-Dihydro-1-(propyl-4-pyridinyl-amino)-2H-indol-2-one | 15.9 |
| 1,3-Dihydro-3,3-dimethyl-1-(propyl-4-pyridinylamino)-2H-indol-2-one | 30.7 |
| Phenobarbital (standard) | 8.4 |

Effective quantities of the compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel™, corn starch and the like; a lubricant such as magnesium strearate or Sterotex®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the target compounds of this invention include:

1,3-Dihydro-1-[ethyl-(3-nitro-4-pyridinyl)amino]-3,3-dimethyl-2H-indol-2-one;

1,3-Dihydro-1-[(3-fluoro-4-pyridinyl)propylamino]-2H-indol-2-one;

1,3-Dihydro-3-methyl-1-(4-pyridinylamino)-2H-indol-2-one;

1,3-Dihydro-3,3-dimethyl-1-(methyl)-4-pyridinylamino)-2H-indol-2-one;

1,3-Dihydro-6-methyl-1-(4-pyridinylamino)-2H-indol-2-one;

1-[(3-Amino-4-pyridinyl)butylamino]-1,3-dihydro-3-methyl2H-indol-2-one;

3-Dihydro-1-[(3-methyl-4-pyridinyl)propylamino]-3-phenylmethyl-2H-indol-2-one;

3,3 -Diethyl-1,3-dihydro-1-[(3-ethyl-4-pyridinyl)amino]-2H-indol-2-one;

1,3-Dihydro-1-[(3-fluoro-4-pyridinyl)-1-(2-propenyl) amino]-2H-indol-2-one;

1,3-Dihydro-3-methyl-1-[(3-methyl-4-pyridinyl)-1-(2-propynyl)amino]-2H-indol-2-one;

1,3-Dihydro-1-[(3-phenylmethyl-4-pyridinyl)amino]-2H-indol-2-one;

1-[(3-Amino-4-pyridinyl)methylamino]-1,3-dihydro-3-propyl-2H-indol-2-one;

1,3-Dihydro-1-(propyl-3-pyridinylamino)-2H-indol-2-one;

1-[(4-Amino-3-pyridinyl)methylamino]-1,3-dihydro-3-propyl-2H-indol-2-one;

1-[(4-Fluoro-3 -pyridinyl)propylamino]-1,3-dihydro-2H-indol-2-one;

1,3-Dihydro-1'-(4-pyridinylamino)spiro[2H-indene-2,3'-[3H]indol]-2'(1'H)-one.

Examples of the novel intermediate compounds of this invention include:

1 -Amino-3,3-bis(4-pyridinylmethyl)-1,3-dihydro-2H-indol-2-one;

1 -Amino-1,3-dihydro-5-methoxy-2H-indol-2-one.

The following examples are for illustrative purposes only and are not to be construed as limiting the invention. All temperatures are given in degrees centigrade (°C.) unless otherwise designated.

EXAMPLE 1

1,3-Dihydro-1-(propyl-4-pyridinylamino)-2H-indol-2-one

To a stirred solution of 1,3-dihydro-1-(propylamino)-2H-indol-2-one (10.4 g) and phenol (30.8 g), preheated to 150° C. under nitrogen, was added 4-bromopyridine hydrochloride (11.04 g) over 5 min. Heating was continued for 7 hours at which time the reaction mixture was cooled to room temperature and made basic by slow addition of dilute aqueous sodium hydroxide. The product was extracted four times with ethyl acetate and the combined organic layers back-extracted with dilute aqueous sodium hydroxide, washed with brine, and dried ($K_2CO_3$). Filtration and concentration gave the crude product. Purification via flash column chromatography (silica gel, EtOAc), preparative high performance liquid chromatography (HPLC) (silica gel, EtOAc-.2% $Et_3N/0$–7% MeOH/EtOAc), and a third column (alumina, EtOAc) followed. Recrystallization from ethyl acetate-pentane afforded 2.10 g (14%) of 1,3-dihydro-1-(propyl-4-pyridinylamino)-2H-indol-2-one, as a solid, m.p. 140°–143° C.

Analysis: Calculated for $C_{16}H_{17}N_3O$: 71.89%C 6.41%H 15.72%N Found: 71.69%C 6.40%H 15.64%N

EXAMPLE 2

1,3-Dihydro-1-(4-pyridinylamino)-2H-indol-2-one

To a stirred solution of 1-amino-1,3-dihydro-2H-indol-2-one (10.0 g) and isopropanol (270 ml) was added 4-chloropyridine hydrochloride (15.21 g). The flask was fitted with a condensor and nitrogen inlet and flushed with nitrogen. The reaction mixture was heated at reflux for 15½ hours. Upon cooling to room temperature, saturated aqueous sodium bicarbonate was added to neutralize the hydrochloride salts. Solid sodium bicarbonate was added until gas evolution ceased. The resulting slurry was mixed with methanol-dichloromethane and filtered. The solids were washed with methanol-dichloromethane and the combined filtrate concentrated. Purification via flash column chromatography (silica gel, 2% $Et_3N/0$→10% MeOH/EtOAc) afforded fractions from which the product crystallized. The mother liquor was concentrated and a second crop of product was obtained. Obtained was 4.81 g (31%) of 1,3-dihydro-1-(4-pyridinylamino)-2H-indol-2-one, as a solid, m.p. 221°–224° C.

Analysis: Calculated for $C_{13}H_{11}N_3O$: 69.32%C 4.92%H 18.65%N Found: 69.20%C 4.91%H 18.64%N

EXAMPLE 3

1,3-Dihydro-1-(3-fluoro-4-pyridinylamino)-2H-indol-2-one

To a stirred solution of 1-amino-1,3-dihydro-2H-indol-2-one (10.03 g) in isopropanol (270 ml) was added 4-chloro-3-fluoropyridine hydrochloride (10.0 g). The flask was flushed with nitrogen and fitted with a reflux condensor and nitrogen inlet. The reaction mixture was heated at reflux for 22 hours. Upon cooling to room temperature, the reaction mixture was poured into dilute aqueous sodium bicarbonate and ethyl acetate. The layers were separated and the aqueous layer extracted twice with ethyl acetate and once with ether. The combined organic layers were washed with brine and dried ($K_2CO_3$). Filtration and concentration gave the crude product.

Purification via preparative high pressure liquid chromatography (HPLC) (silica gel, 3% MeOH/DCM) followed by trituration with ether-pentane afforded 4.4 g (30%) of 1,3-dihydro-1-(3-fluoro-4-pyridinylamino)-2H-indol-2-one as a solid, m.p. 181°–183° C.

Analysis: Calculated for $C_{13}H_{10}FN_3O$: 64.19%C 4.14%H 17.27%N Found: 64.10%C 4.09%H 17.25%N

EXAMPLE 4

1,3-Dihydro-3,3-dimethyl-1-(propyl-4-pyridinylamino)-2H-indol-2-one

To a stirred solution of 1-amino-1,3-dihydro-3,3-dimethyl-2H-indol-2-one (7.35 g) and isopropanol (167 ml) was added 4-chloropyridine hydrochloride (8.15 g). The flask was flushed with nitrogen and fitted with a condensor and nitrogen inlet. The reaction mixture was heated at reflux for 9 hours. Upon cooling to room temperature, the reaction mixture was poured into dilute aqueous sodium bicarbonate. The product was extracted thrice with ethyl acetate and once with dichloromethane. The combined organic layers were washed with brine and dried ($K_2CO_3$). Filtration and concentration gave the crude product. Purification via flash column chromatography (silica gel, 2% $Et_3N/0$-2% MeOH/ether) afforded 3.5 g (33%) of the desired product.

To a solution consisting of the above product (3.36 g) and dimethylformamide (120 ml), cooled to 0° C. under nitrogen, was added sodium hydride (0.36 g, 97% dry). Stirring was continued at 0° C. for 35 min at which time bromopropane (1.3 ml) was added dropwise. The reaction mixture was allowed to slowly warm over 1½ hours, then poured into ethyl acetate and water. The layers were separated and the aqueous layer extracted with ethyl acetate. The combined organic layers were back-washed with water, and dried ($K_2CO_3$). Filtration and concentration gave the crude product. Purification via flash column chromatography (silica gel, 2% $Et_3N$/0-1% MeOH/ether) afforded 3.5 g (87%) of 1,3-dihydro-3,3-dimethyl-1-(propyl-4-pyridinylamino)-2H-indol-2-one, m.p. 125°-127° C.

Analysis: Calculated for $C_{18}H_{21}N_3O$: 73.19%C 7.17%H 14.23%N Found: 73.33%C 7.20%H 14.20%N

EXAMPLE 5

1,3-Dihydro-1-[(3-fluoro-4-pyridinyl)amino]-3-methyl-2H-indol-2-one hemifumarate To a stirred solution of 1-amino-1,3-dihydro-3-methyl-2H-indol-2-one (8.40 g) and isopropanol (230 ml) was added 4-chloro-3-fluoropyridine hydrochloride (9.59 g). The flask was flushed with nitrogen, fitted with a reflux condensor and nitrogen inlet, and the mixture heated at reflux for 17.5 hours. Additional 4-chloro-3-fluoropyridine hydrochloride (4.36 g) was added and heating was continued for 6.25 hours. Upon cooling to room temperature, the mixture was poured into dilute aqueous sodium bicarbonate and dichloromethane-methanol. The layers were separated and the aqueous layer was extracted with dichloromethane and the combined organic layers were washed with brine and dried ($K_2CO_3$). Filtration and concentration gave the crude product.

Purification via flash column chromatography (silica gel, 2% triethylamine/ether) afforded 5.40 g. The product was re-purified on another column. The hemi-fumarate was prepared in absolute ethanol with 1.0 eq of fumaric acid. Filtration afforded 1,3-dihydro-1-[(3-fluoro-4-pyridinyl)amino]-3-methyl-2H-indol-2-one hemifumarate, as a salt, m.p. 202°-202.5° C.

Analysis: Calculated for $C_{14}H_{12}FN_3O \cdot 60.94\%C$ 4.48%H 13.33%N 0.5 $C_4H_4O_4$: Found: 60.73%C 4.36%H 13.21%N

EXAMPLE 6

1,3-Dihydro-1-(propyl-4-pyridinylamino)-3-spiro-1'-cyclopentan-2H-indol-2-one

To a stirred solution of 1-amino-1,3-dihydro-1'-cyclopentan-2H-indol-2-one (9.6 g) and isopropanol (189 ml) was added 4-chloropyridine hydrochloride (8.1 g). The flask was flushed with nitrogen and fitted with a condenser and nitrogen inlet. The reaction mixture was heated at reflux for 17 hours. Upon cooling to room temperature, the reaction mixture was poured into dilute aqueous sodium bicarbonate. The product was extracted with ethyl acetate (6x). The combined organic layers were washed with brine and dried ($K_2CO_3$). Filtration and concentration gave the crude product. Purification via flash chromatography (silica gel, 2% triethylamine/0-2% methanol/ether) afforded 4.4 g of the desired product.

To a solution of the above product (4.4 g) and DMF (143 ml), cooled to 0° C. under nitrogen, was added sodium hydride (0.42 g, 97% dry). Stirring was continued at 0° C. for 20 minutes at which time bromopropane (1.6 ml) was added dropwise. The reaction mixture was allowed to slowly warm over 1 hour, then poured into ethyl acetate and water. The layers were separated and the aqueous phase extracted with ethyl acetate (3x). The combined organic layers were washed with brine and dried ($K_2CO_3$). Filtration and concentration gave the crude product.

Purification via flash column chromatography (2% triethylamine/0-1% methanol/ether) afforded 4.6 g of the desired product. Recrystallization from ether—petroleum ether gave 1,3-dihydro-1-(propyl-4-pyridinylamino)-3-spiro-1'-cyclopentan-2H-indol-2-one, m.p. 91°-93° C.

Analysis: Calculated for $C_{20}H_{23}N_3O$: 74.74%C 7.21%H 13.07%N Found: 74.92%C 7.39%H 13.13%N

EXAMPLE 7

1,3-Dihydro-3,3-dimethyl-1-[4-(3-fluoropyridinyl)-propylamino]2H-indol-2-one

To a stirred solution of 1-amino-1,3-dihydro-3,3-dimethyl-2H-indol-2-one (6.0 g) and isopropanol (136 ml) was added 4-chloro-3-fluoropyridine hydrochloride (4.41 g). The flask was flushed with nitrogen, fitted with a reflux condensor and nitrogen inlet, and the mixture heated at reflux for 20 hours. Upon cooling to room temperature, the reaction mixture was poured into dilute aqueous sodium bicarbonate and dichloromethane. The layers were separated and the organic layer washed with water (2x). The combined aqueous layers were back-extracted with dichloromethane and the combined organic layers washed with brine and dried ($K_2CO_3$). Filtration, concentration, and purification by flash column chromatography (silica gel, 2% triethylamine/ether), and another column (silica gel, 0.50% ethyl acetate/hexane) afforded 2.12 g of the desired intermediate.

To a solution consisting of the above product (2.12 g) and DMF (71 ml), cooled to 0° C. under nitrogen, was added sodium hydride (0.21 g, 97% dry). Stirring was continued at 0° C. for 35 minutes at which time bromopropane (0.78 ml) was added dropwise. The reaction mixture was allowed to warm slowly over 1.5 hours, then poured into ethyl acetate and water. The layers were separated and the aqueous layer extracted with ethyl acetate (3-4x). The combined organic layers were backed-extracted with water (3x), brine, and dried ($K_2CO_3$). Filtration, concentration, and purification via flash chromatography (silica gel, 25-50% ethyl acetate/hexane) afforded 1.80 g of the desired product. Recrystallization from pentane gave 1,3-dihydro-3,3-dimethyl-1-[4-(3-fluoropyridinyl)propylamino]2H-indol-2-one, m.p. 65°-67° C.

Analysis: Calculated for $C_{18}H_{20}FN_3O$: 68.99%C 6.43%H 13.41%N Found: 68.99%C 6.36%H 13.44%N

EXAMPLE 8

1-Amino-1,3-dihydrospiro[2H-indene-2,3'-[3H]-indol]-2'(1'H)one

To a slurry consisting of 1,3-dihydro-1-[(phenylmethylene)amino]-spiro[2H-indene-2,3'-[3H]indole]-2'(1'H)one (13.8 g), and absolute ethanol (300 ml) was added hydrazine hydrate (13.9 ml). The resulting mixture was heated at reflux for 3 hours, cooled to room temperature and the resulting precipitate removed by filtration. The mother liquor was concentrated and the resulting oil solidified upon addition of ethyl acetate-hexane. The resulting solid was recovered by filtration. Additional product was obtained from the mother liquor as above. Recrystallization from ethyl acetate afforded 1-amino-1,3-dihydrospiro[2H-indene-2,3'-[3H]-indol]-2'(1'H)one, m.p. 195°-197° C.

Analysis: Calculated for $C_{16}H_{14}N_2O$: 76.78%C 5.64%H 11.19%N Found: 76.33%C 5.54%H 11.06%N

EXAMPLE 9

1-Amino-3,3-bis(4-pyridinylmethyl)-1,3-dihydro-2H-indol-2-one

To a solution consisting of 3,3-bis-(4-pyridinylmethyl)-1,3-dihydro-1-[(phenylmethylene)amino]-2H-indol-2-one (7.84 g) and absolute ethanol (68 ml) was added hydrazine hydrate (6.4 ml). The resulting mixture was heated at reflux for 5.75 hours, followed by cooling to 0° C. The product crystallized upon cooling. Filtration and washing with ether-pentane afforded 2.50 g of 1-amino-3,3-bis(4-pyridinylmethyl)-1,3-dihydro-2H-indol-2-one.

Analysis: Calculated for $C_{20}H_{18}N_4O$: 72.71%C 5.49%H 16.69%N Found: 72.17%C 5.41%H 16.77%N

EXAMPLE 10

3,3-Bis(4-pyridinylmethyl)-1,3-dihydro-1-(propyl-4-pyridinylamino)-2H-indol-2-one To a stirred solution of 1-amino-3,3-bis(4-pyridinylmethyl)-1,3-dihydro-2H-indol-2-one (2.85 g) and phenol (5.74 g), preheated to 155° C. with stirring was added 4-chloropyridine hydrochloride (1.30 g) and p-toluenesulfonic acide•$H_2O$ (150 mg). After 5 minutes of heating, additional 4-chloropyridine hydrochloride (2.60 g) was added. Heating was continued at 155° C. for 1¾ hours. The mixture was cooled to room temperature, dissolved in dilute aqueous sodium bicarbonate and dichloromethane, and the layers separated. The layers were separated and the organic layer washed with dilute aqueous sodium bicarbonate. The combined aqueous layers were back-extracted with dichloromethane and the combined organic layers washed with brine and dried ($K_2CO_3$). Filtration, concentration, and purification (silica gel, 2% triethylamine/0–30% methanol/ether) gave 2.20 g of the desired intermediate.

To a solution consisting of the above product (2.89 g) and DMF (50 ml), cooled to 0° C. under nitrogen, was added sodium hydride (0.19 g, 97% dry). Stirring was continued at 0° C. for 20 minutes at which time bromopropane (0.68 ml) was added dropwise. The reaction mixture was allowed to warm to room temperature, poured into water, and the product extracted with ether and dried ($K_2CO_3$). Filtration and concentration gave the product which was recrystallized from ethyl acetate affording 1.85 g of 3,3-bis(4-pyridinylmethyl)-1,3-dihydro-1-(propyl-4-pyridinylamino)-2H-indol-2-one, m.p. 182°–184° C.

Analysis: Calculated for $C_{28}H_{27}N_5O$: 74.81%C 6.05%H 15.58%N Found: 74.98%C 6.12%H 15.57%N

EXAMPLE 11

1.3-Dihydro-1'-(propyl-4-pyridinylamino)spiro-[2H-indene-2,3'-[3H]indol]-2'(1'H)-one To a stirred solution of 1-amino-1,3-dihydrospiro[2H-indene-2,3'[3H]indol]-2'(1'H)-one (2.84 g) and isopropanol (45 ml) was added 4-chloropyridine hydrochloride (1.88 g). The flask was flushed with nitrogen, fitted with a reflux condenser and nitrogen inlet, and the mixture heated at reflux for 17 hours. Upon cooling to room temperature, the reaction mixture was poured into dilute aqueous sodium bicarbonate and dichloromethane. The layers were separated and the organic layer washed with water (2×). The combined aqueous layers were back-extracted with dichloromethane and the combined organic layers washed with brine and dried ($K_2CO_3$). Filtration and concentration afforded the crude intermediate.

A flask containing the intermediate (11.4 mmol) was flushed with nitrogen and DMF (114 ml) was added. Upon cooling to 0° C. under nitrogen, sodium hydride (0.37 g, 97% dry) was added with stirring. After 10 minutes, bromopropane (1.36 ml) was added dropwise. The reaction mixture was allowed to warm slowly to room temperature, then poured into water and ethyl acetate. The layers were separated and the aqueous layer extracted with ethyl acetate (3×). The combined organic layers were washed with water, brine, and dried ($K_2CO_3$). Filtration, concentration, and purification via flash column chromatography (silica gel, 2% triethylamine/ether) afforded 2.50 g of 1,3-dihydro-1'-(propyl-4-pyridinylamino)spiro[2H-indene-2,3'-[3H]indol]-2'(1'H)-one, m.p. 159°–161° C.

Analysis: Calculated for $C_{24}H_{23}N_3O$: 78.02%C 6.27%H 11.37%N Found: 78.02%C 6.33%H 11.35%N

EXAMPLE 12

1'Methyl-1-(propyl-4-pyridinylamino)spiro-[3H-indole-3,4'-piperidin]-2(1 H)-one

To a stirred solution consisting of 1-amino-1'-methylspiro [3H-indole-3,4'-piperidin]-2(1H)-one (3.77 g), phenol (11.1 g), and p-toluenesulfonic acid hydrate (0.10 g), heated at 150° C., was added 4-chloropyridine hydrochloride (2.45 g). Additional 4-chloropyridine hydrochloride (2.45 g) was added after 25 minutes and again (0.73 g) after an additional 75 minutes. The reaction mixture was stirred an additional 40 minutes, cooled to room temperature, and poured into dichloromethane and dilute aqueous sodium bicarbonate. The layers were separated and the aqueous layer extracted twice with dichloromethane and once with ether. The combined organic layers were washed with water and brine, and dried ($K_2CO_3$). Filtration and concentration afforded the crude product. Purification via flash column chromatography (silica gel, 2% triethylamine/0–20% methanol/ethyl acetate) afforded 4.40 g of the desired intermediate.

To a solution consisting of the above intermediate (4.40 g) and DMF (130 ml) cooled to 0° C. under nitrogen was added sodium hydride (0.39 g, 97% dry). Stirring was continued at 0° C. for 25 minutes at which time bromopropane (1.42 ml) was added dropwise. The reaction mixture was allowed to warm to room temperature, stirred an additional 2 hours, then poured into water and ethyl acetate. The layers were separated and the aqueous layer extracted with ethyl acetate (3×) and ether (1×). The combined organic layers were washed with water (2×), brine, and dried ($K_2CO_3$). Filtration, concentration, and purification via flash column chromatography (silica gel, 2% triethylamine/0–20% methanol/ethyl acetate) afforded 4.17 g of the desired product. Decolorization with activated carbon in ethyl acetate gave 1'methyl-1-(propyl-4-pyridinylamino)spiro[3H-indole-3,4'-piperidin]-2(1H)-one, as a solid, m.p. 125°–127° C.

Analysis: Calculated for $C_{21}H_{26}N_4O$: 71.97%C 7.48%H 15.99%N Found: 71.64%C 7.41%H 15.85%N

EXAMPLE 13

1,3-Dihydro-1-[(3-fluoro-4-pyridinyl)-propylamino]-2H-indol-2-one

To a stirred solution consisting of 1,3-dihydro-1-propylamino-2H-indol-2-one (5.06 g), phenol (13.2 g) and p-toluenesulfonic acid hydrate (0.25 g), heated at 150° C., was added 4-chloro-3-fluoropyridine hydrochloride (5.37 g). Heating was continued at 150° C. for 10.75 hours at which time additional 4-chloro-3-fluoropyridine (2.05 g) was added and heating continued an additional 6.5 hours. Upon cooling to room temperature, the reaction mixture was dissolved in dichloromethane and dilute aqueous sodium bicarbonate. The layers were separated and the organic layer extracted with dilute aqueous sodium bicarbonate (2×). The combined aqueous layers were back-extracted with dichloromethane and ether. The combined organic layers were washed with brine, dried ($K_2CO_3$), filtered, and concentrated. Purification via flash column chromatography (silica gel, 2% triethylamine/ether) and another column (silica gel, EtOAc) afforded the desired product as a solid.

The reaction was repeated with the amine (6.09 g) and 4-chloro-3-fluoropyridine hydrochloride (6.00 g) in phenol (13.6 g) and heated for 17.5 hours. The reaction mixture was treated as above and combined with the above product. Recrystallization from ether/pentane afforded 1.20 g of 1,3-dihydro-1-[(3-fluoro-4-pyridinyl)propylamino]-2H-indol-2-one, as a solid, m.p. 113.5°–115.5° C.

Analysis: Calculated for $C_{16}H_{16}FN_3O$: 67.35%C 5.65%H 14.73%N Found: 67.20%C 5.67%H 14.71%N

EXAMPLE 14

1,3-Dihydro-5-methoxy-1-(4-pyridinylamino)-2H-indol-2-one

A solution consisting of 1-amino-1,3-dihydro-5-methoxy-2H-indol-2-one (5.00 g), 4-chloropyridine hydrochloride (4.00 g), and 1-methyl-2-pyrrolidinone (40 ml) was heated in a 105° C. oil bath for 2 hours after which time more 4-chloropyridine hydrochloride (0.21 g) was added and heating was continued an additional 1 hour. Upon cooling to room temperature, dilute aqueous sodium bicarbonate and ethyl acetate were added. The layers were separated and the aqueous layer extracted with ethyl acetate (3×). The combined organic layers were washed with water, brine, and dried ($K_2CO_3$). Filtration and oncentration gave the crude product.

Purification via flash column chromatography (silica gel, 2% triethylamine/0–20% methanol/ethyl acetate) and another column (silica gel, 2% triethylamine/0–5% imethanol/ethyl acetate) afforded 2.4 g of the desired product as an oil. Dissolution in ethyl acetate followed by addition of ether gave 1,3-dihydro-5-methoxy-1-(4-pyridinylamino)-2H-indol-2-one, as a solid, m.p. 169°–171° C.

Analysis: Calculated for $C_{14}H_{13}N_3O_2$: 65.87%C 5.13%H 16.46%N Found: 65.62%C 5.15%H 16.15%N

EXAMPLE 15

1-Amino-1,3-dihydro-5-methoxy-2H-indol-2-one

5-Methoxy-2-nitrophenyl acetic acid (40 g) was reduced in a Parr Hydrogenation Apparatus as an aqueous sodium hydroxide solution (15.2 g of 50% aq. NaOH diluted to 170 ml with distilled water) with 10% Pd-C (2.00 g) at a pressure of 65 psig hydrogen. Upon no further uptake of hydrogen, the catalyst was removed by filtration through a pad of celite. The resulting solution was treated with sodium nitrite (13.37 g) and cooled in a 0° C. water bath. This solution was added slowly to conc. hydrochloric acid (144 ml) with stirring at a rate so as to maintain an internal temperature of <+15° C. The resulting mixture was stirred an additional 20 minutes while cooling to 0°–20° C.

To a solution consisting of stannous chloride monohydrate (129.5 g) and conc. hydrochloric acid (130 ml) stirred in a 0° C. ice bath was added the above mixture over about 10 minutes. Stirring was continued for 45–60 minutes after addition, after which time, the resulting precipitate was recovered by filtration. The precipitate was air dried, then slurried in water (345 ml) and heated to reflux. Upon cooling to room temperature, the reaction mixture was basified (pH 12) by addition of aqueous sodium hydroxide. The product was extracted with dichloromethane (3×) and the combined organic layers washed with brine and dried ($K_2CO_3$). Filtration and partial concentration gave the analytical sample. Further concentration afforded 15.0 g of 1-amino-1,3-dihydro-5-methoxy-2H-indol-2-one, as a solid, m.p. 136–138.

Analysis: Calculated for $C_9H_{10}N_2O_2$: 60.67%C 5.66%H 15.72%N Found: 60.66%C 5.65%H 15.64%N

We claim:

1. A compound of the formula

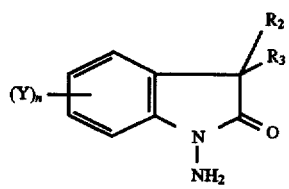

where $R_2$ and $R_3$ are independently aryl or arylloweralkyl; Y is hydrogen, halogen, hydroxy, loweralkyl, loweralkoxy, nitro, amino, or trifluoromethyl; n is an integer of 1 to 3, or a pharmaceutically acceptable acid addition salt thereof or where applicable, an optical, geometrical or stereoisomer or racemic mixture thereof.

2. A pharmaceutical composition for enhancing memory which comprises an effective memory enhancing amount of a compound as defined in claim 1 and a pharmaceutically acceptable carrier therefor.

3. A method of treating a mammal in need of memory enhancement which comprises administering to a mammal a memory enhancing effective amount of a compound of the formula

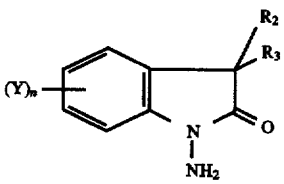

where $R_2$ and $R_3$ are independently hydrogen, loweralkyl, aryl, or arylloweralky; Y is hydrogen, halogen, hydroxy, loweralkyl, loweralkoxy, nitro, amino, or trifluoromethyl; n is an integer of 1 to 3, or a pharmaceutically acceptable acid addition salt thereof or where applicable, an optical, geometrical or stereoisomer or racemic mixture thereof.

* * * * *